US006129671A

United States Patent [19]
Hastings

[11] Patent Number: 6,129,671
[45] Date of Patent: Oct. 10, 2000

[54] DIAGNOSTIC MEDICAL ULTRASOUND IMAGING SYSTEM AND ULTRASOUND REVIEW STATION WITH A BIOPHYSICAL INPUT DEVICE

[75] Inventor: Jeffrey S. Hastings, Los Altos, Calif.

[73] Assignee: Acuson Corporation, Mountain View, Calif.

[21] Appl. No.: 09/239,665

[22] Filed: Jan. 29, 1999

[51] Int. Cl.[7] .................................................. A61B 8/00
[52] U.S. Cl. ............................................................ 600/437
[58] Field of Search ................................. 600/300, 407, 600/437

[56] References Cited

U.S. PATENT DOCUMENTS

| | | | |
|---|---|---|---|
| 4,993,068 | 2/1991 | Piosenka et al. | 380/23 |
| 5,335,288 | 8/1994 | Faulkner | 382/4 |
| 5,544,654 | 8/1996 | Murphy et al. | 600/443 |
| 5,730,124 | 3/1998 | Yamauchi | 600/300 |
| 5,851,186 | 12/1998 | Wood et al. | 600/437 |
| 5,853,367 | 12/1998 | Chalek et al. | 600/437 |
| 5,930,804 | 7/1999 | Yu et al. | 707/104 |
| 5,986,662 | 11/1999 | Argiro et al. | 345/424 |

*Primary Examiner*—Francis J. Jaworski
*Attorney, Agent, or Firm*—Brinks Hofer Gilson & Lione

[57] ABSTRACT

An ultrasound imaging system and ultrasound review station with a biophysical detector are provided. A biophysical attribute of a user is used to authorize (i.e., identify and authenticate) the user. Because the identification and authentication procedures are combined into a single step, the time and effort required for an authorized user to gain access to the ultrasound imaging system or ultrasound review station is greatly reduced. Using a biophysical attribute also makes the system or station practically impervious to impostors since biophysical attributes are unique and virtually impossible to duplicate. Also, since a user cannot forget or lose a biophysical attribute, the risk that an authorized user will be denied access is eliminated.

18 Claims, 2 Drawing Sheets

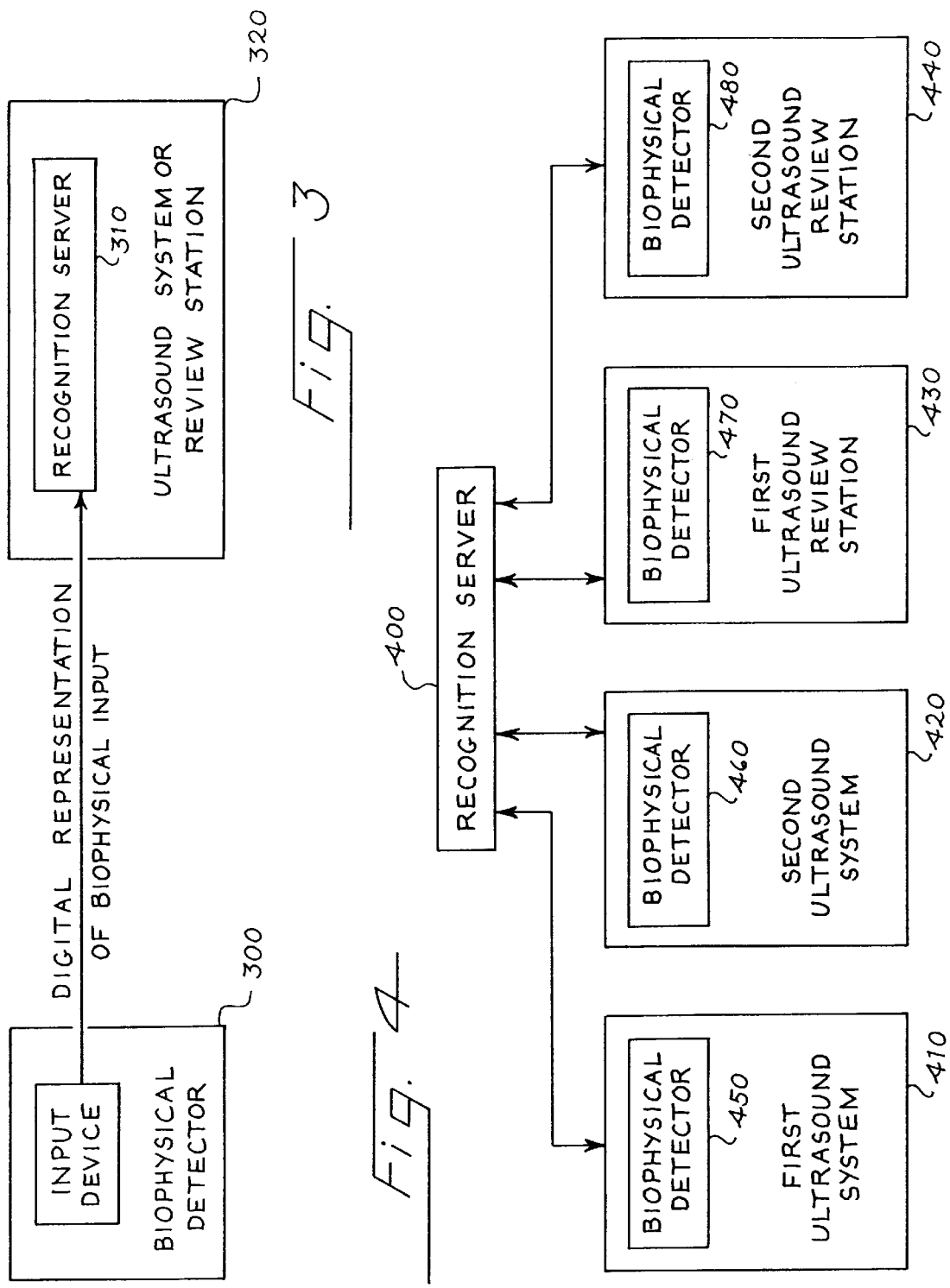

DIAGNOSTIC MEDICAL ULTRASOUND IMAGING SYSTEM AND ULTRASOUND REVIEW STATION WITH A BIOPHYSICAL INPUT DEVICE

BACKGROUND

Current ultrasound imaging systems and ultrasound review stations use a variety of security measures to prevent unauthorized users from gaining access. The most common security measures use a two-step approach of identification and authentication to authorize a user. First, a user attempting to gain access identifies himself, typically by typing a user-id or by using a magnetically-encoded card. After identifying himself, the user provides authentication information, usually in the form of a password or personal identification number (PIN). If the authentication information is verified, the user is granted access.

This two-step approach of identification and authentication has several disadvantages associated with it. First, this method is slow and tedious. Every time a user wants to access an ultrasound system or ultrasound review station, he must first manually enter his identification information and then manually enter his authentication information. This process can be very tedious for users who frequently access an ultrasound imaging system or ultrasound review station or who access several devices in an ultrasound network. Additionally, this method only provides a limited amount of security. For example, if a person obtains an authorized user's user-id and password, that unauthorized person can gain access. Conversely, if an authorized user forgets his user-id or password, he will be denied access.

There is, therefore, a need for an improved ultrasound imaging system and ultrasound review station that will overcome these disadvantages

SUMMARY

The present invention is defined by the following claims, and nothing in this section should be taken as a limitation on those claims.

By way of introduction, the preferred embodiments described below include an ultrasound imaging system and ultrasound review station with a biophysical detector. With these preferred embodiments, a biophysical attribute of a user is used to authorize (i.e., identify and authenticate) the user. Because the identification and authentication procedures are combined into a single step, the time and effort required for an authorized user to gain access to the ultrasound imaging system or ultrasound review station is greatly reduced. Using a biophysical attribute also makes the system or station practically impervious to impostors since biophysical attributes are unique and virtually impossible to duplicate. Also, since a user cannot forget or lose a biophysical attribute, the risk that an authorized user will be denied access is eliminated.

The preferred embodiments will now be described with reference to the attached drawings.

BRIEF DESCRIPTION OF THE DRAWINGS

FIG. 3 is a block diagram of a biophysical detector of a preferred embodiment coupled with an ultrasound imaging system or ultrasound review station having a recognition server.

FIG. 4 is a block diagram of a recognition server of a preferred embodiment coupled with a plurality of ultrasound imaging systems and ultrasound review stations with biophysical detectors.

DETAILED DESCRIPTION OF THE PRESENTLY PREFERRED EMBODIMENTS

Figure 1:
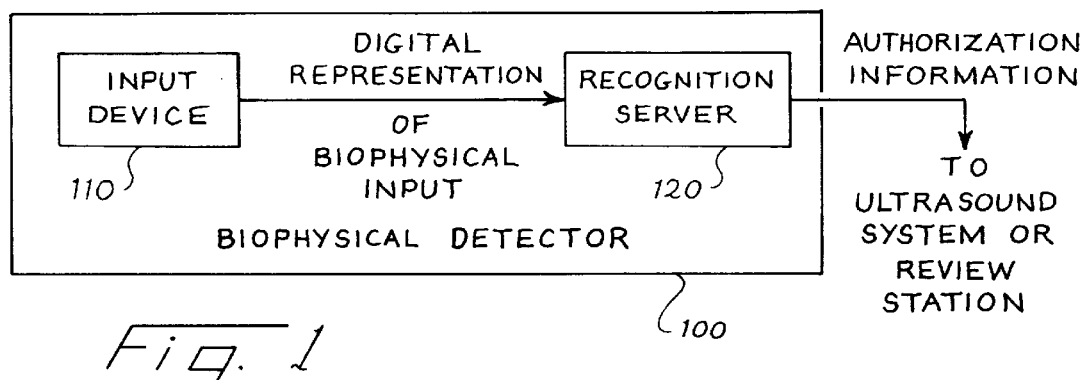
FIG. 1 is a block diagram of a biophysical detector of a preferred embodiment.
Figure 2:
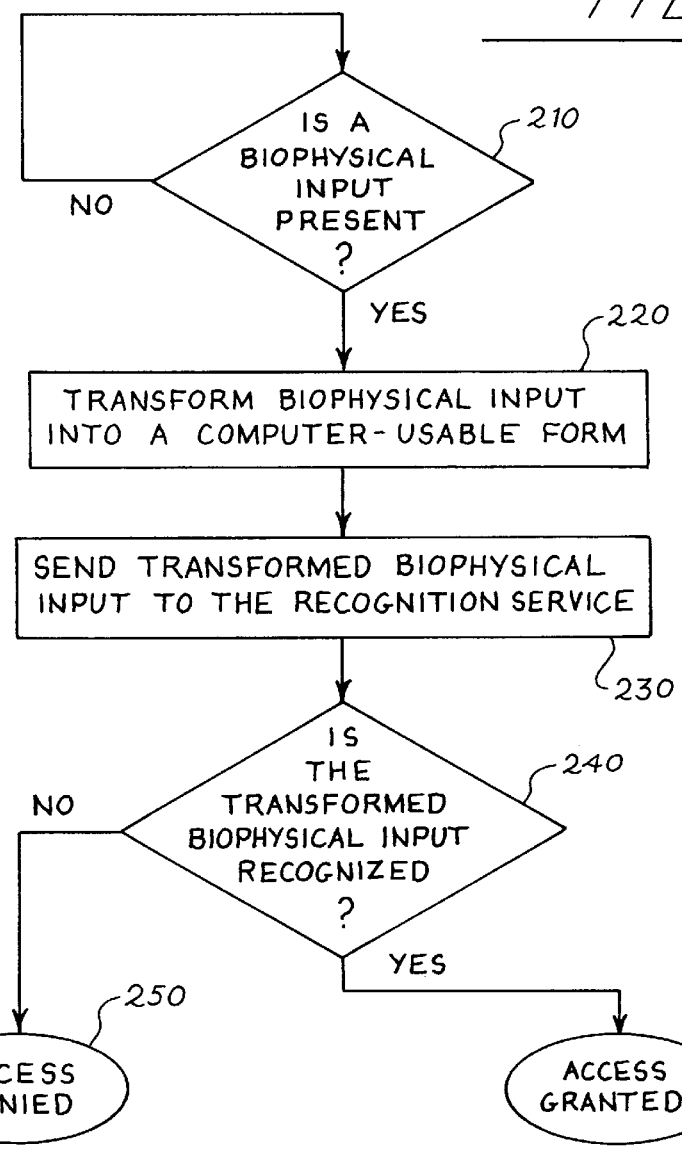
FIG. 2 is a flow chart of a preferred method for authorizing a user to use a diagnostic medical ultrasound imaging system or ultrasound review station.

Turning now to the drawings, FIG. 1 is a block diagram of a biophysical detector 100 of a preferred embodiment. As shown in FIG. 1, the biophysical detector 100 comprises a biophysical input device 110 coupled with a recognition server 120. As used herein, the term "coupled with" means directly coupled with or indirectly coupled with through one or more components. The biophysical detector 100 can be coupled with an ultrasound imaging system or ultrasound review station to grant an authorized user access to the ultrasound imaging system or ultrasound review station, as shown in the flow chart of FIG. 2 and as described below.

To gain access to an ultrasound imaging system or ultrasound review station coupled with the biophysical detector 100, the user first provides the biophysical detector 100 with a biophysical input compatible with the input device 110. For example, if the input device 110 is a fingerprint detector, the user would place his finger on the input device 110. Once the biophysical input is detected (step 210), the biophysical input is transformed into a computer-usable form (step 220) and sent to the recognition server 120 for analysis (step 230). For example, a fingerprint detector can transmit light to the user's finger, and reflections from the ridges and valleys of the finger can be converted to a digital signal. The recognition server can use the reflections to form an image of the user's fingerprint and can compare this image (or calculations based on this image) to those of authorized users. If the fingerprint is recognized (step 240), the biophysical detector 110 provides authorization information to the ultrasound imaging system or ultrasound review station to grant access to the user (step 260). If the fingerprint is not recognized, the user is denied access (step 250).

There are several advantages associated with this embodiment. By using a biophysical attribute to identify and authenticate a user, the authorization process is quickly accomplished in a singe step, reducing the time and effort required to access the ultrasound imaging system or ultrasound review station. Also, because a biophysical attribute is unique and virtually impossible to duplicate, the biophysical detector 100 makes the ultrasound imaging system or ultrasound review station practically impervious to impostors. Additionally, with the biophysical detector 100, the risk that an authorized user will be denied access is eliminated since a user cannot forget or lose a biophysical attribute.

In the embodiment shown in FIG. 1, the recognition server 120 is part of the biophysical detector 100. One advantage associated with this embodiment is that all of the components needed to authorize a user are located in the biophysical detector 100. To benefit from the computing power of the ultrasound imaging system or ultrasound review station, the recognition server 310 can be located in the ultrasound system or ultrasound review station 320 instead of the biophysical detector 300, as shown in FIG. 3.

In another embodiment, the recognition server is part of an ultrasound network coupled with one or more ultrasound imaging systems and/or ultrasound review stations. FIG. 4 a block diagram of one such network in which a central recognition server 400 is coupled with a first and second ultrasound system 410, 420 and a first and second ultrasound review station 430, 440, each with its own biophysical detector 450, 460, 470, 480. With this embodiment, a user receives the benefits of biophysical authorization regardless of which network device he is using. This finds particular utility when a user accesses networked ultrasound imaging systems or ultrasound review stations at different locations.

For simplicity, the term "recognition server" is used in the specification and claims to broadly refer to the hardware and/or software components that are used to analyze a signal representative of a user's biophysical attribute to determine whether the user is authorized to gain access to an ultrasound imaging system or ultrasound review station. For example, a recognition server can comprise a dedicated processor or can be a general controller or processor of an ultrasound imaging system or ultrasound review station running a biophysical attribute recognition application. It is important to note that any appropriate software language and any appropriate hardware, analog or digital, can be used and that the recognition server can be implemented exclusively with hardware.

Also for simplicity, the term "biophysical attribute" is used in the specification and claims to broadly refer to any biological or behavioral property that can be used to identify a person. Preferably, a biophysical attribute is an attribute that is associated with only one person, although it can also include attributes that occur with a sufficiently small frequency in a population to be considered effectively unique. Examples of biophysical attributes include, but are not limited to, a fingerprint, a hand print, a retina print, a voice print, a handwriting sample (such as the user's signature), an image of a user's physical feature (such as the user's face), or any other kind of biological or behavioral property. It is important to note that biophysical attributes can be used individually or in combination for additional security. For example, a retina scan can be performed while the user is signing his name, and both the retina print and signature can be used to authenticate the user. The widest variety of devices can be used as a biophysical detector, including, but not limited to, a fingerprint detection device, a hand print detection device, a retina scanner, a microphone, a handwriting input pad and stylus, and an analog or digital camera.

Lastly, the term "ultrasound review station" is used in the specification and claims to broadly refer to any node (e.g., device) on an ultrasound network. For example, an ultrasound review station can be a workstation that is able to view ultrasound images transferred through an ultrasound network that couples the review station with an ultrasound imaging system or digital mass storage device. It is important to note that an ultrasound review station does not necessarily display ultrasound images. For example, an ultrasound review station can be a workstation coupled with the ultrasound network that allows a physician or technician to generate or modify an ultrasound examination report without viewing ultrasound images.

The foregoing detailed description has described only a few of the many forms that this invention can take. Of course, many changes and modifications are possible to the preferred embodiments described above. For this reason it is intended that this detailed description be regarded as an illustration and not as a limitation of the invention. It is only the following claims, including all equivalents, that are intended to define the scope of this invention.

What is claimed is:

1. A diagnostic medical ultrasound imaging system comprising:

a biophysical detector operative to detect a biophysical attribute of a user; and a recognition server coupled with the biophysical detector and operative to uniquely identify the user based on the detected biophysical atribute and to enable local access of the diagnostic medical ultrasound imaging system in response to the detected biophysical attribute being recognized by the recognition server.

2. A diagnostic medical ultrasound review station comprising:

a biophysical detector operative to detect a biophysical attribute of a user; and a recognition server coupled with the biophysical detector and operative to uniquely identify the user based on the detected biophysical atribute and to enable lical acess of the diagnostic medical ultrasound review station in response to the detected biophysical attribute being recognized by the recognition server.

3. A diagnostic medical ultrasound imaging network comprising:

a plurality of ultrasound devices, each comprising a respective biophysical detector operative to detect a biophysical attribute of a user, each of said plurality being selected from the group consisting of a diagnostic medical ultrasound imaging system and a diagnostic medical ultrasound review station; and a recognition server coupled with said plurality of ultrasound devices and operative to uniquely identify the user based on the detected biophysical attribute and to enable local access of one of said plurality of ultrasound devices in response to the detected biophysical attribute being recognized by the recognition server.

4. The invention of claim 1, 2, or 3, wherein the biophysical detector comprises a fingerprint detection device.

5. The invention of claim 1, 2, or 3, wherein the biophysical detector comprises a hand print detection device.

6. The invention of claim 1, 2, or 3, wherein the biophysical detector comprises a retina scanner.

7. The invention of claim 1, 2, or 3, wherein the biophysical detector comprises a microphone.

8. The invention of claim 1, 2, or 3, wherein the biophysical detector comprises a handwriting input pad and stylus.

9. The invention of claim 1, 2, or 3, wherein the biophysical detector comprises a camera.

10. A method for enabling local access of a diagnostic medical ultrasound imaging system, the method comprising:

(a) detecting a biophysical attribute of a user, the biophysical attribute uniquely identifying the user;

(b) uniquely identifying the user based on the detected biophysical attribute;

(c) enabling local access of the diagnostic medical ultrasound imaging system in response to the detected biophysical attribute being recognized.

11. A method for enabling local access of a diagnostic medical ultrasound review station, the method comprising:

(a) detecting a biophysical attribute of a user, the biophysical attribute uniquely identifying the user;

(b) uniquely identifying the user based on the detected biophysical attribute;

(c) enabling local access of the diagnostic medical ultrasound review station in response to the detected biophysical attribute being recognized.

12. The method of claim 10 or 11, wherein (a) comprises receiving a fingerprint from a user.

13. The method of claim 10 or 11, wherein (a) comprises receiving a hand print from a user.

14. The method of claim 10 or 11, wherein (a) comprises receiving a retina print from a user.

15. The method of claim 10 or 11, wherein (a) comprises receiving a voice print from a user.

16. The method of claim 10 or 11, wherein (a) comprises receiving a handwriting sample from a user.

17. The method of claim 10 or 11, wherein (a) comprises receiving an image of a physical feature of a user.

18. The method of claim 17, wherein (a) comprises receiving an image of the user's face.

* * * * *